United States Patent

Campbell et al.

[11] Patent Number: 5,502,250
[45] Date of Patent: Mar. 26, 1996

[54] BIS(DIALKYLTHIOPHOSPHORYL)AMINES AS METAL EXTRACTANTS

[75] Inventors: John Campbell, Rochdale; Raymond F. Dalton, Cheadle Hulme; Peter M. Quan, Rochdale, all of United Kingdom

[73] Assignee: Zeneca Limited, London, England

[21] Appl. No.: 348,997

[22] Filed: Nov. 29, 1994

Related U.S. Application Data

[62] Division of Ser. No. 70,951, Jun. 4, 1993, Pat. No. 5,393,431.

[30] Foreign Application Priority Data

Jun. 5, 1992 [GB] United Kingdom ............... 9211906
Feb. 5, 1993 [GB] United Kingdom ............... 9302332

[51] Int. Cl.$^6$ .................................................. C07F 9/36
[52] U.S. Cl. ............................................................. 564/12
[58] Field of Search ................................. 558/155, 157; 564/12

[56] References Cited

U.S. PATENT DOCUMENTS

| | | | |
|---|---|---|---|
| 2,798,086 | 7/1957 | Coover, Jr. et al. | 558/157 X |
| 3,231,637 | 1/1966 | Nielson | 558/157 |
| 3,966,569 | 6/1976 | Reinhardt et al. | 423/100 |
| 4,226,791 | 10/1986 | Reinhardt et al. | 423/139 |
| 5,028,334 | 7/1991 | Rickelton et al. | 210/638 |
| 5,135,652 | 8/1993 | Boateng | 210/638 |

FOREIGN PATENT DOCUMENTS 210387 1/1987 European Pat. Off. .
400311 12/1990 European Pat. Off. .

OTHER PUBLICATIONS

O. Navratil et al., Darstellung von Tetraphenylestern der Imidothio–und . . . , Z. Chem. vol. 24, No. 1, 1984, p. 30.
J. Boedeker, Zur Lage Der P=S–Valenzschwingung und . . . , J. Organometal. Chem., vol. 56, 1973, pp. 255–260.
A. Schmidpeter et al., Chem. Ber., vol. 101, 1968 pp. 815–823.
Zabirov, N. G. et al. *Chemical Abstracts* vol. 116, 41584; *Zh. Obshch. Khim.* 1991, 61(6), 1474–1475.

*Primary Examiner*—Johann Richter
*Assistant Examiner*—Michael G. Ambrose
*Attorney, Agent, or Firm*—Cushman Darby & Cushman

[57] ABSTRACT

A process for extracting metal values especially zinc values from aqueous solutions of metal salts which comprises contacting the aqueous solution with an organic phase comprising a compound of the formula:

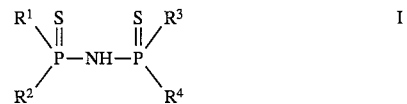

wherein each of $R^1$, $R^2$, $R^3$ and $R^4$, independently, represents an optionally substituted hydrocarbyl or hydrocarbyloxy group or $R^1$ and $R^2$ together with the attached phosphorus atom and/or $R^3$ and $R^4$ together with the attached phosphorus atom form a 5- to 8-membered heterocyclic ring.

5 Claims, No Drawings

BIS(DIALKYLTHIOPHOSPHORYL)AMINES AS METAL EXTRACTANTS

This is a division of application Ser. No. 08/070,951, filed Jun. 4, 1993, now U.S. Pat. No. 5,393,431.

This invention relates to a chemical process and more particularly to a solvent extraction process for extracting metal values from aqueous solutions of metal salts and also to metal extractants which may be used in said process.

The use of solvent extraction techniques for the hydrometallurgical recovery of metal values from metal ores has been practised commercially for a number of years. In general, the technique involves contacting an aqueous solution of metal salt, obtained for example by treating the crushed ore with acid, with a solution in a water-immersible organic solvent of an organic extractant which complexes with the metal and extracts it into the non-aqueous phase. The metal may then be recovered by a further extraction step in which the organic solution containing the metal complex is contacted with another aqueous phase containing an agent, usually a strong acid, capable of decomposing the complex so that the metal is extracted into the aqueous phase from which it can be recovered by suitable procedures such as electrowinning.

Since metals are usually found in their ores in association with other metals, it is essential that the organic extractant extracts the desired metal selectively so as to achieve a degree of separation from the other metals present. Selective extractants are known for some metals, for example copper, and their use is well-established. The search for a suitably selective extractant for zinc has been less successful.

The use of extractants containing the phosphoric acid group, especially di(2-ethylhexyl)phosphoric acid (D2EPHA), has been proposed, see "Productivity and Technology in the Metallurgical Industries", edited by M. Koch and J. C. Taylor, in an article by A. Selke and D. de Juan Garcia, pages 695 to 703. However, as is apparent from the Selke et al article, ferric iron is extracted together with the zinc. To prevent build-up of the ferric iron in the organic solution, it is necessary to remove the iron from the organic solution in a stripping stage subsequent to that used to recover the zinc. In this separate stripping stage, the organic solution is contacted with 5 to 6 molar hydrochloric acid to give ferric chloride in hydrochloric acid. Free hydrochloric acid is recovered by a further step in which the ferric chloride in hydrochloric acid is contacted with an organic solution containing tributyl phosphate from which the ferric chloride is stripped using water. The additional stages required to remove iron add to the complexity and cost of the procedure and hence are undesirable.

The behaviour of bis(2,4,4-trimethylpentyl) monothiophosphinic acid as an extractant for zinc has been studied by C. Caravaca and F. J. Alguacil (Hydrometallurgy, 27, 1991, 327–338) who found that at relatively acidic pH values (near 1.0) the proportion of zinc extracted was only slightly higher than the proportion of iron.

It has now been found that compounds containing the amidobis(thiophosphoryl) group are excellent metal extractants, particularly for the separation of other metals from solutions containing iron. In particular, it has been found that amidobis(thiophosphoryl) compounds are highly effective in selectively extracting zinc from acidic aqueous solutions containing both zinc (II) and iron (III) ions. It has also been found that certain of the amido-bis(thiophosphoryl) compounds are strong extractants, that is that they extract zinc from aqueous solutions at pH values below 2 without requiring the addition of base to neutralise the protons liberated by the complexation reaction.

Accordingly, the present invention provides a process for extracting metal values from aqueous solutions of metal salts which comprises contacting the aqueous solution with an organic phase comprising a compound of the formula:

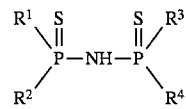

wherein each of $R^1$, $R^2$, $R^3$ and $R^4$, independently, represents an optionally substituted hydrocarbyl or hydrocarbyloxy group or $R^1$ and $R^2$ together with the attached phosphorus atom and/or $R^3$ and $R^4$ together with the attached phosphorus atom form a 5- to 8-membered heterocyclic ring.

It will be appreciated that the structure of the compounds of Formula I is such that they may exist in more than one tautomeric form, another such form having the structure:

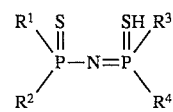

wherein $R^1$–$R^4$ are as already defined. Whilst the invention is described herein with reference to compounds of Formula I, it is to be understood that it relates to said compounds in any of their possible tautomeric forms.

Optionally substituted hydrocarbyl and optionally substituted hydrocarbyloxy groups which may be represented by $R^1$, $R^2$, $R^3$ and $R^4$ comprise optionally substituted alkyl, alkoxy, aryl and aryloxy groups including any combination of these, for example optionally substituted aralkyl and alkaryl groups.

As examples of optionally substituted alkyl and alkoxy groups which may be represented by $R^1$, $R^2$, $R^3$ and $R^4$, there may be mentioned groups in which the alkyl or alkoxy moieties each contain from 1 to 20, for example from 1 to 10, carbon atoms. As examples of optionally substituted aryl and aryloxy groups, there may be mentioned optionally substituted phenyl and phenoxy groups.

As examples of heterocyclic rings which may be formed by $R^1$ and $R^2$ together with the attached phosphorus atom and/or by $R^3$ and $R^4$ together with the attached phosphorus atom, there may be mentioned rings wherein $R^1$ and $R^2$ together and/or $R^3$ and $R^4$ together have the following structures:

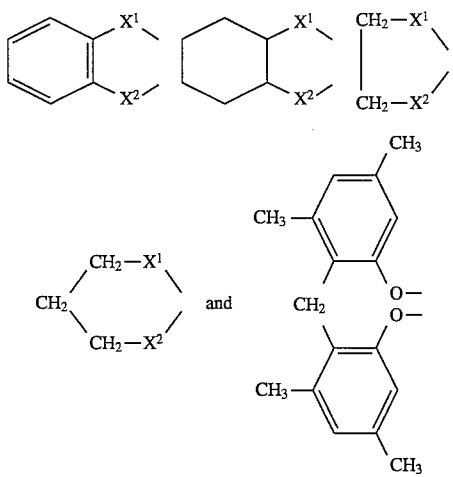

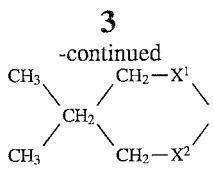

wherein each of $X^1$ and $X^2$, independently, represents O or S and in which one or more of the carbon atoms may optionally carry substituents.

When any of $R^1$, $R^2$, $R^3$ and $R^4$ are substituted hydrocarbyl or hydrocarbyloxy groups or when the derived heterocyclic rings carry substituents, said substituents should be such as do not adversely effect the ability of the compounds of Formula I to complex with metals, particularly zinc. Suitable substituents include halogen, nitro, cyano, hydrocarbyloxy, hydrocarbyloxycarbonyl, acyl and acyloxy and there may be more than one substituent in which case the substituents may be the same or different.

A preferred class of compounds of Formula I for use in the process of the invention includes compounds wherein each of $R^1$, $R^2$, $R^3$ and $R^4$ is an alkyl group, especially a secondary alkyl group. Good solubility in preferred solvents is provided when $R^1$, $R^2$, $R^3$ and $R^4$ taken together contain at least 16, and preferably at least 20, saturated aliphatic carbon atoms. For this purpose, a phenyl or phenoxy group may be regarded as equivalent to about two or three saturated aliphatic carbon atoms. In an especially preferred compound of Formula I, each of $R^1$, $R^2$, $R^3$ and $R^4$ is 2-pentyl.

Surprisingly, it has been found that for extraction of zinc, the strength of the extractant increases with increased branching of the alkyl groups at the point of junction with phosphorus. Thus where $R^1$–$R^4$ are all primary alkyl groups, the extractants are weak, showing low extraction of zinc at pH values below 2. If $R^1$–$R^4$ are secondary alkyl groups such as 2-butyl or 2-pentyl groups, or alternatively $R^1$ and $R^3$ are primary alkyl groups but $R^2$ and $R^4$ are tertiary alkyl groups such as tert-butyl, the extractants have satisfactory strength. If $R^1$ and $R^3$ are secondary alkyl and $R^2$ and $R^4$ are tertiary alkyl, the extractants are very strong and it becomes more difficult to strip the metal from the extractant. For ease of manufacture it is preferred that $R^1$ is the same as $R^2$ and $R^3$ is the same as $R^4$ and especially preferred that $R^1$–$R^4$ are secondary alkyl groups such as cyclohexyl or substituted cyclohexyl, norbornyl and particularly 2-pentyl groups.

A second preferred class of compounds of Formula I is that in which at least one and especially at least two of $R^1$ to $R^4$ are optionally substituted phenoxy groups, particularly alkyl substituted phenoxy groups wherein the alkyl groups contain from 1 to 20, for example from 1 to 10, carbon atoms such as 2-tert-butyl-4-methylphenoxy, 4-tert-butylphenoxy and 2,4-dimethylphenoxy. This group of compounds, especially the sub-group in which all four of $R^1$ to $R^4$ are optionally substituted phenoxy groups, is preferred for both ease of synthesis and because it has been found that they generally have faster rates of extraction than some of the equivalent alkyl and aryl substituted compounds.

Compounds of Formula I may be obtained from a chlorophosphorus compound of formula A, B, C or D

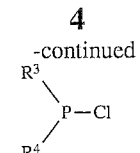

A

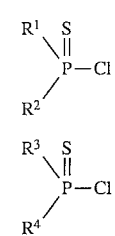

When $R^1$–$R^4$ are identical alkyl or aryl groups, the chloro compound of formula A or B may be reacted with hexamethyldisilazane and then with sulphur as described by Robert D. Bereman et al, J. Am. Chem. Soc., 98, 7266, 1976.

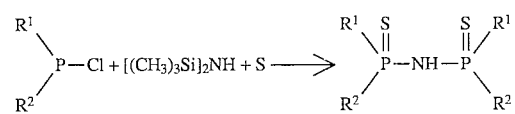

Alternatively, a chloro compound of formula C or D may be reacted with an excess of ammonia to give a phosphoramide, E.

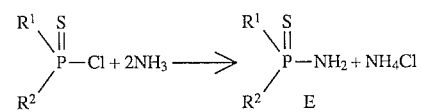

When $R^1$ and $R^2$ are alkyl or aryl groups, it may be possible to heat the amide yielding the required product with elimination of ammonia. However, it is preferred, especially when $R^1$ or $R^2$ or $R^3$ or $R^4$ are alkoxy or aryloxy groups, to react the amide E with chloro compound C or D in the presence of a strong base.

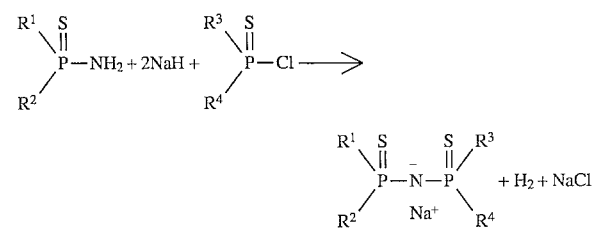

Instructions for the preparation of amides (cf E) and reaction with chloro compounds for oxygenated analogues are given by L. Meznik and A. Maracek, Z. Chem. 21(8), 1981 at page 259, but more satisfactory reaction conditions are provided herein.

General methods for preparation of the chloro compounds A–D are well known to the art, for example when $R^1$–$R^4$ are alkyl or aryl groups, Grignard reagents may be reacted with phosphorus trichloride (if required in two stages, to give a mixed product) as described by W. Voskuil and J. F. Arens, Rec. Trav. Chim., 82, 302, (1963):

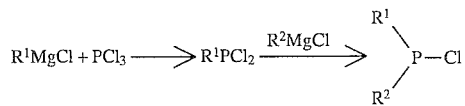

Alternatively, 3 equivalents of a Grignard reagent may be reacted with a dialkyl phosphite to give a dialkyl phosphine oxide which is converted into the acid chloride by reaction with phosphorus trichloride as described by Robert H Williams and Lyle A Hamilton, J. Am. Chem. Soc., 74, 5418, 1952.

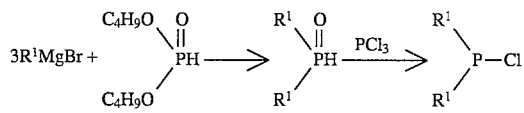

Useful available compounds of formula A or B include chlorodiphenylphosphine.

To prepare compounds of formulae C and D in which $R^1$ and $R^2$ are alkoxy or aryloxy, a dithiophosphoric acid may be reacted with chlorine or sulphuryl chloride:

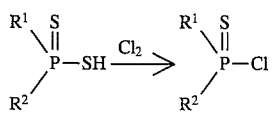

as described by John H. Fletcher et al, J. Am. Chem. Soc., 72, 2461, 1950.

Where $R^1$–$R^4$ are alkoxy or aryloxy groups, a wide range of dithiophosphoric acids for use in the reaction above may be prepared by reaction of the appropriate alcohol or phenol either with phosphorus pentasulphide or with thiophosphoryl chloride in the presence of an acid acceptor.

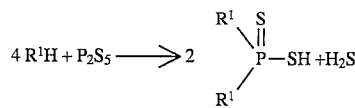

(Fletcher, loc cit)

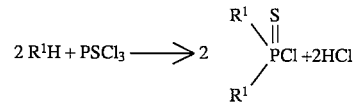

See N. A. Meinhardt, S. Z. Cardon and P. W. Vogel, J. Org. Chem., 25, 1991, (1960) and J. H. Fletcher et al, J. Am. Chem. Soc., 70, 3943, (1948).

Compounds of formula C in which $R^1$ is phenyl and $R^2$ is aryloxy may be obtained by reacting $C_6H_5PSCl_2$ with a phenol.

The aforementioned compounds of formulae C and D in which $R^1$–$R^4$ are hydrocarbyl groups containing an alkyl or cycloalkyl residue may be prepared by the reaction of phosphine with alkyl halides or, preferably, by the radical catalysed addition of phosphine to certain olefins to form secondary phosphines which may then be converted via the corresponding dithiophosphinic acids to the compounds of formulae C and D. It is preferred to use olefins in which the double bond is not at a terminal carbon atom in order to provide structures C and D in which $R^1$–$R^4$ are secondary alkyl groups. The olefin addition may be represented as follows, $R_5$ and $R_6$ being alkyl groups:

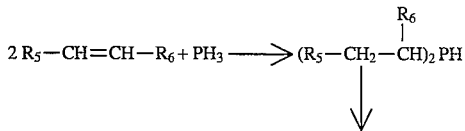

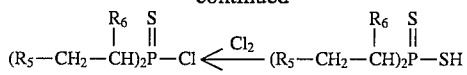

Reaction between the olefin and the phosphine is typically performed at a temperature of about 80°–150° C. in the presence of a free radical catalyst such as azobis-isobutyronitrile. Depending upon the reaction conditions, the constitution of the olefin and the stoichiometric ratio of the reactants, the main product can be a primary or secondary phosphine. Primary phosphines may, if desired, be reacted with a different olefin to provide secondary phosphines containing two different alkyl groups. Examples of suitable olefins include 2-butene, 2-pentene, 2-methyl-2-butene, 2-octene, cyclohexene, norbornene, 1,5-cyclooctadiene (which reacts with phosphine to give predominantly a mixture of 9H-9-phosphabicyclo[4.2.1]nonane and 9H-9-phosphabicyclo[3.3.1]nonane), 1,5-dimethyl-1,5-cyclooctadiene and dicyclopentadiene. Mixtures of commercially available olefins are particularly useful.

The organic phase employed in the process of the invention typically contains a water-immiscible inert organic solvent, that is to say a water-immiscible organic liquid that is inert under the extraction conditions and is a good solvent for the extractant compound of Formula I and the metal complex thereof.

It will be appreciated that the process of the invention may be incorporated into a wide variety of different procedures for the recovery of metals from their ores or from other metal-bearing sources. Details of these procedures will vary depending on the metal concerned and the nature and composition of the leach solution. An integrated process which is especially suitable for sulphate leach solutions can be carried out using operations well known to the skilled person.

Typically, the process of the invention comprises a sequence of stages in which the metal is extracted into an organic solution, stripped into an aqueous phase and recovered from the aqueous phase by any suitable means, for example by electrowinning.

Thus, as a particular aspect of the invention, there is provided a process for extracting metal values from aqueous solution by a sequence of stages comprising:

(1) contacting the aqueous solution containing metal values with a solution of an extractant compound of Formula I in a water-immiscible organic solvent whereby to extract metal values into the solvent in the form of a complex of the metal with the extractant;

(2) separating the solvent phase containing metal complex from the extracted aqueous phase;

(3) contacting the solvent phase containing metal complex with an aqueous strip solution whereby the metal complex is unstable and metal ions transfer into the aqueous phase, and (4) separating the aqueous phase containing metal ions from the stripped solvent phase.

The process of the invention may be applied to the extraction from aqueous solution of any metal capable of forming a stable complex with a compound of Formula I in the organic phase. The process is especially suitable, for the solvent extraction of zinc from aqueous solutions of zinc salts, especially solutions obtained by the acid leaching of zinc ores. Examples, however, of other metals which can be extracted from acidic solutions having pH values of pH 2 and below are bismuth, cadmium, silver, mercury and copper but many other metals may also be extracted at higher pH values.

In operating stage (1) of the aforementioned process, the amount of extractant compound of Formula I to be used will depend upon the concentration of metal salt in the aqueous solution and also on the plant design. It is preferred, however, to use from 5 g to 300 g of compound of Formula I per dm$^3$ (liter) of organic solution. Higher concentrations may be used but tend to afford organic phases of too high viscosity for convenient handling. Lower concentrations can also be used but involve the use of unnecessarily large volumes of solvent.

For use with aqueous solutions containing 1 g or more per dm$^3$ of a metal such as zinc, it is preferred to use from 20 to 200 g of compounds of Formula I per dm$^3$ of organic solution. If desired, the compound of Formula I can be used together with an agent which modifies the behaviour thereof in the extraction process, for example an alcohol or ester which may be used in an amount of from 10% to 200%, especially from 20% to 100%, by weight of compound of Formula I. It has been found that for some of the pure compounds of Formula I the rate at which zinc is extracted is rather slow, but that a wide range of compounds may be added to increase this rate even in amounts of 1.0% and below. Useful rate increasing additives include compounds which are known to be extractants for zinc and are soluble in the organic phase but with fast rates of extraction including compounds of Formula I wherein $R^1$–$R^4$ include aryloxy or alkyloxy groups. Other compounds found to be effective in this aspect are other known zinc extractants such as esters of phosphoric acid, (eg DEHPA), and particularly surface active agents capable of transferring metal ions such as alkyl and aryl sulphonic acids having solubility in the organic phase.

Stages (1) and (2) of the aforementioned process may conveniently be carried out using well known conventional solvent extraction techniques. Typically, the aqueous solution containing metal values is intimately contacted, in a single stage or in multiple stages but preferably continuously, with the organic phase (for example by agitating the two phases together in a suitable vessel) for a time sufficient to allow substantial extraction of the metal values from the aqueous solution, the two phases then being separated in any conventional manner. The extraction is usually carried out at ambient temperature although somewhat higher temperatures, for example up to 100° C. but preferably not more than 50° C., may be used if operationally convenient.

Organic solvents which may be used in the extraction include any mobile organic solvent, or mixture of solvents, which is immiscible with water and is inert under the extraction conditions to the other materials present. Examples of suitable solvents include aliphatic, alicyclic and aromatic hydrocarbons and mixtures of any of these as well as chlorinated hydrocarbons such as trichloroethylene, perchloroethylene, trichloroethane and chloroform. Preferred solvents are hydrocarbon solvents including high flash point solvents with a high aromatic content such as SOLVESSO 150 commercially available from Exxon (SOLVESSO is a trade mark) and AROMASOL H which consists essentially of a mixture of trimethylbenzenes and is commercially available from Imperial Chemical Industries PLC (AROMASOL is a trade mark). Especially preferred, however, on grounds of low toxicity and wide availability are hydrocarbon solvents of relatively low aromatic content such as kerosene, for example ESCAID 100 which is a petroleum distillate comprising 20% aromatics, 56.6% paraffins and 23.4% naphthenes commercially available from Exxon (ESCAID is a trade mark).

The conditions under which the solvent extraction is performed are chosen to suit the metal or metals present in the aqueous solution. It is generally desirable that conditions are selected such that any other metals present do not form stable complex compounds with the compound of Formula I in order that substantially only the desired metal is extracted from the aqueous solution. Since formation of the complex may involve the liberation of acid, it may be necessary to add, for example, alkali during the process to maintain the pH within a desired range but it is generally preferred to avoid this, especially in a continuously-operated process. It is a particular advantage of the process of the invention that zinc can be extracted selectively even in the presence of iron.

Stages (3) and (4) of the process may conveniently be carried out by intimately contacting the solution of metal complex in the organic solvent obtained in stage (2) with an aqueous solution of a mineral acid at a suitable temperature, the two phases then being separated in conventional manner. The operations are usually performed at ambient temperature although somewhat higher temperatures, for example up to 100° C. but preferably not more than 50° C., may be used if operationally convenient.

The aqueous strip solution used in stage (3) preferably contains sulphuric acid, suitable strengths being from 100 to 250 g of acid per dm$^3$ of solution. After removal of a convenient part of the metal by, for example, electrolysis, the recovered aqueous acid, containing residual metal salt, may be re-used in stage (3) of the process. The extractant compound of Formula I regenerated in stage (3) may be recycled for use in stage (1).

Suitable relative volumes of organic to aqueous phases are those conventionally used in metal extraction processes and in the stripping stage will be typically not more than 10:1. The stripped organic layer, containing regenerated compound of Formula I and some residual metal, may be re-used in stage (1) of the process. The aqueous layer from stage (4), containing metal salt, may be treated in any conventional manner to obtain the metal.

Compounds of Formula I wherein $R^1=R^2=R^3=R^4=$methyl, phenyl or phenoxy have been reported in the literature (Inorg. Chem., 1980, 19, 1672–1680) but not in connection with a solvent extraction process. The other compounds of Formula I are believed to be novel.

Accordingly, in a further aspect, the invention provides a compound of the formula:

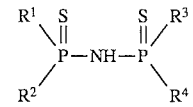

wherein each of $R^1$, $R^2$, $R^3$ and $R^4$, independently, represents an optionally substituted hydrocarbyl or hydrocarbyloxy group or $R^1$ and $R^2$ together with the attached phosphorus atom and/or $R^3$ and $R^4$ together with the attached phosphorus atom form a 5- to 7-membered heterocyclic ring provided that when $R^1$, $R^2$, $R^3$ and $R^4$ are identical, $R^1$ is not methyl, phenyl or phenoxy.

Preferred compounds of the invention include compounds of Formula I wherein each of $R^1$, $R^2$, $R^3$ and $R^4$ is a branched alkyl group, especially a secondary alkyl group, for example 2-pentyl and compounds wherein $R^1$, $R^2$, $R^3$ and $R^4$ taken together contain at least 16, and preferably at least 20, saturated aliphatic carbon atoms.

Further preferred compounds of the invention include compounds of Formula I wherein at least one and especially at least two of $R^1$ to $R^4$ are optionally substituted phenoxy groups and more especially those compounds wherein each of $R^1$, $R^2$, $R^3$ and $R^4$ is a substituted phenoxy group, especially an alkyl substituted phenoxy group. The alkyl substituents may typically contain from 1 to 20, for example from 1 to 10, carbon atoms.

The invention is illustrated but not limited by the following Examples.

EXAMPLE 1

This Example illustrates the preparation and utility of the compound N-(diphenylphosphinothioyl)-P,P-diphenylphosphinothioic amide (1) for the separation of zinc and iron.

The general synthetic procedure adopted was that described by F. T. Wang et al in Synthetic Reactions in Metal-Organic Chemistry, 1978, 8 (2), 119–125, with the modification that all reactions were carried out under a blanket of nitrogen gas. 1,1,1,3,3,3-Hexamethyldisilazane (43.6 g) from The Aldrich Chemical Company was added in portions to a stirred solution of chlorodiphenylphosphine (120 g), from Fluka Chemicals, in toluene (400 cm$^3$) at ambient temperature. Precipitation of a white solid and a slight exotherm was observed during the addition. The reaction mixture was then stirred and heated at 90° C. for 3 hours whereupon any solid material redissolved. The by-product chlorotrimethylsilane and the toluene were subsequently removed by distillation. The reaction mixture was cooled to 25° C. and elemental sulphur (17.3 g) added portionwise, with stirring. A slight exotherm was observed with each addition. When addition of the sulphur was complete, the reaction temperature was raised to 85°–90° C. and maintained at this level for 3 hours before cooling to ambient temperature (25° C.). The resulting white precipitate was isolated by filtration, triturated with hexane (300 cm$^3$.), filtered, the filter cake washed with hexane and dried. The mass spectrum of this solid and titration with perchloric acid in acetic acih and acetic anhydride, confirmed that it comprised 95% by weight N-(diphenylphosphinothioyl)-P,P-diphenyl phosphinothioic amide, a compound of Formula I in which $R^1=R^2=R^3=R^4$=phenyl. It was used as an extractant without any further purification.

The ability of this compound (1) to extract zinc selectively from a solution containing a mixture of zinc and ferric ions in sulphate solution was investigated by the following general method hereinafter designated Test 1.

TEST 1

An aqueous solution was prepared which contained 5 gpl zinc and 7 gpl ferric iron as their respective sulphates at pH 1.70. Equal volume portions of this solution and a 0.2 molar solution of the product to be tested, in chloroform or ESCAID 100, were stirred together vigorously for a period of one hour. The organic and aqueous phases were then allowed to separate and the organic phase was analysed for zinc and iron content by inductively coupled plasma spectrophotometry. The results are listed in Table 1.

The results show that the product of this Example extracts zinc with a high degree of selectivity over ferric iron.

The amount of zinc which could be extracted from an aqueous solution of zinc sulphate when the extraction was allowed to proceed to equilibrium was investigated by the following general method hereinafter designated Test 2.

TEST 2

A 0.2 molar solution of the product to be tested was made up in chloroform or ESCAID 100 (as listed in Table 2) and shaken vigorously with an equal volume of a 0.1 molar aqueous solution of zinc sulphate containing sufficient sulphuric acid to give an initial pH value of 2.0. Equal volume samples of the organic and aqueous phases were withdrawn periodically and the aqueous samples were analysed for zinc until it was found that transfer of zinc from the aqueous phase to the organic phase no longer altered with time. The concentrations of zinc then extracted into the organic solutions are listed in Table 2. In all cases 95% of the equilibrium value was reached in less than 5 hr.

The results show that the product of this Example is a strong extractant for zinc at pH 2.

EXAMPLE 2

This Example illustrates the preparation and utility of the compound N-(diisopropylphosphinothioyl)- P,P-diisopropylphosphinothioic amide (2). Following the general synthetic method described in Example 1 above, 1,1,1,3,3,3-hexamethyldisilazane (8.1 g) was reacted under nitrogen with chlorodiisopropylphosphine (15.3 g) in toluene (50 cm$^3$) at 90° C. for 3 hours with removal of chlorotrimethylsilane by distillation. The reaction mixture was cooled to ambient temperature (25° C.) before adding elemental sulphur (3.2 g) portionwise, with stirring. When addition was complete, the reaction temperature was raised to 90° C., for 2 hours before cooling back to ambient temperature. The reaction mixture was allowed to stand at ambient temperature overnight. The resulting white precipitate was isolated by filtration, washed with hexane and dried. The mass spectrum of this solid confirmed its structure as N-(diisopropylphosphinothioyil)-P,P-diisopropyl phosphinothioic amide, a compound of Formula I in which $R^1=R^2=R^3=R^4$=isopropyl. It was used as an extractant without any further purification.

The behaviour of this product as an extractant for zinc was investigated by the general methods of Tests 1 and 2 described in Example 1. The results show that the product of this Example extracts zinc selectively in the presence of iron and that it is a strong extractant for zinc at pH 2.

EXAMPLE 3

A solution of 2-ethylhexyl magnesium bromide was prepared in the usual manner by dissolving 2-ethylhexyl bromide (231.6 g) and magnesium turnings (28.8 g) in tetrahydrofuran (500 cm$^3$). The solution was stirred at 15° C. while a solution of dibutyl phosphite (77.6 g) in diethyl ether (500 cm$^3$) was added during 45 min. The solution was boiled under reflux for 1 hr. and then cooled and 25% aqueous sulphuric acid (500 cm$^3$) was added at such a rate that the temperature did not rise above 15° C. The mixture was stirred for 15 min. and the organic layer was separated and successively extracted with 500 cm$^3$ amounts of; water, water, 15% aqueous sodium bicarbonate solution, and water. The organic solution was distilled yielding bis(2-ethylhexyl)phosphine oxide (58.5 g), b.p. 123° C. at a pressure of 0.1 mm of mercury. This compound (57.0 g) was dissolved in phosphorus trichloride (300 cm$^3$) and the solution was stirred at ambient temperature under nitrogen for 24 hr. and then twice distilled yielding chloro bis(2-ethylhexyl)phosphine (44 g), b.p. 123° C. at a pressure of 0.2 mm of mercury. This compound (29.5 g) was added to a solution of hexamethyldisilazane (8.05 g) in toluene (80 cm$^3$) and the solution was stirred and heated at 90° C. for 3 hr with distillation of chlorotrimethylsilane. The solution was cooled to 20° C., sulphur (3.2 g) was added and the mixture was reheated to 90° C. for 3 hr. It was filtered and the solvents were evaporated under reduced pressure leaving N-[bis(2-ethylhexyl)phosphinothioyl] P,P-bis(2-ethylhexyl) phosphinothioic amide (26.0 g) as an oil ($^{31}$P NMR in CDCl$_3$, multiplet 67 ppm doomfield from H$_3$PO$_4$:MS m/z 593). The compound was too weakly acidic to be titrated with sodium hydroxide in 50% tetrahydrofuran—water so the titration was repeated in the presence of zinc sulphate when an inflection due to complexation with zinc was observed at pH 4.8. From this titre the purity was calculated to be 55% of theoretical based on MW 593. The purity was increased to 80% of theoretical by chromatography on silica gel (supplied by W. R. Grace Ltd., Grade SG/62) using hexane/ethyl acetate as the eluent.

The ability of this compound of Formula I in which $R^1=R^2=R^3=R^4=$2-ethylhexyl to extract zinc selectively from a solution containing zinc and ferric ions in sulphate solution was investigated by the general method of Test 1 described in Example 1 with the difference that the pH of the aqueous solution was initially adjusted to 1.9. The results show that the product of this Example is a weak extractant for zinc at pH 1.9 but that it extracts zinc selectively in the presence of iron and has good solubility in ESCAID 100.

EXAMPLE 4

Following the procedure of Example 3, 1-bromopentane (181.2 g) was used as starting material to prepare di-n-pentylphosphine oxide (22.4 g), and this compound was further reacted with phosphorus trichloride to give chloro di-n-pentylphosphine, b.p. 88° C. at a pressure of 0.3 mm of mercury. This compound (10.4 g) was added to a solution of hexamethyldisilazane (4.02 g) in dry toluene (10 cm$^3$) under nitrogen, and the solution was heated at 100° C. for 5 hr. with distillation of chlorotrimethylsilane. The solution was cooled to 25° C. and sulphur (1.6 g) was added causing the temperature to rise to 60° C. The solution was heated to 100° C. for 4 hr. and then allowed to cool. Work up as described in Example 3 gave a crude product (10.6 g) which was also titrated in the presence of zinc and found to have a purity of 55% of theoretical (in this case based on MW 425). Further purification by chromatography on silica gel using hexane with increasing amounts of ethyl acetate (0–30% by volume) as eluent gave N-(di-n-pentylphosphinothioyl)-P,P-di-n-pentylphosphinothioic amide (2.4 g) of 95% purity, m.p. 59°–63.5° C. (MS:m/z 426, $^{31}$P NMR in CDCl$_3$, singlet 68.3 ppm downfield of H$_3$PO$_4$). The compound of Formula I in which $R^1=R^2=R^3=R^4=$n-pentyl was tested by the procedure of Test 1. The results show that the product of this Example is a weak extractant for zinc at pH 1.7 but that it extracts zinc selectively in the presence of iron and has good solubility in ESCAID 100.

EXAMPLE 5

A Grignard solution prepared from 2-bromopentane (227.3 g, 1.5 moles) and magnesium (39.6 g) in tetrahydrofuran (500 cm$^3$) was estimated by a standard procedure and found to contain 1.05 moles of 2-pentyl magnesium bromide. The solution was diluted with diethyl ether (250 cm$^3$) and cooled to 10° C. in an atmosphere of nitrogen. A solution of dibutyl phosphate (67.9 g, 0.35 moles) in diethyl ether (500 cm$^3$) was added with stirring during 1 hr. whilst the temperature was maintained at 10°–15° C. The solution was then boiled under reflux for ten min. to complete the reaction. The solution was cooled to 10° C. and 25% aqueous sulphuric acid (500 cm$^3$) was added with stirring during 1 hr. The organic layer was separated and successively extracted with water (two 300 cm$^3$ amounts), 10% aqueous sodium bicarbonate (300 cm$^3$), and water (two 300 cm$^3$ amounts). It was then dried (magnesium sulphate) and filtered and distilled yielding di-2-pentylphosphine oxide (35.0 g), b.p. 110° C. at a pressure of 0.8 mm of mercury. All of this compound was stirred in nitrogen atmosphere with phosphorus trichloride (50 cm$^3$) at 22° C. After 1 hr. it was found by gas chromatography that about 20% remained unreacted; a second addition of phosphorus trichloride (10 cm$^3$) was made and stirring was continued for a further 2 hr. when reaction had reached about 95% completion. The solution was distilled yielding volatile phosphorus compounds and finally chloro di-2-pentylphosphine (27.5 g), b.p. 72°–74° C. under a pressure of 1.5 mm of mercury.

Chloro di-2-pentylphosphine (27.0 g) was stirred under nitrogen in an apparatus set for distillation. Hexamethyldisilazane (10.5 g) was added and the solution was heated at 100° C. for 18 hr. during which time chlorotrimethylsilane distilled. The solution was cooled to 22° C. and diluted with toluene (50 cm$^3$) and sulphur (4.16 g) was added. Addition of sulphur caused the temperature of the mixture to rise to 80° C. The mixture was stirred and heated at 100° C. for 4 hr. and then cooled and filtered. The toluene was distilled and the last traces of volatile materials were removed by heating the residue at 60° C. under a pressure of 0.5 mm of mercury for 30 min. The residue was N-(di-2-pentylphosphinothioyl)-P,P-di-2-pentylphosphinothioic amide (2.4 g) (MS:m/z 426. $^{31}$P NMR in CDCl$_3$:multiplet, 84.4 ppm downfield of H$_3$PO$_4$). The purity was determined by titration of a sample dissolved in 50% tetrahydrofuran—water solution with 0.1M aqueous sodium hydroxide solution for the acidic (NH or SH) proton which was 50% neutralised at pH 9.4:by this method the purity was found to be 85% of theoretical based on M. W. 425. The product of Formula I in which $R^1=R^2=R^3=R^4=$2-pentyl was examined as an extractant for zinc by Test 1 and 2 with the results listed in Tables 1 and 2 respectively, which show that it is a strong extractant for zinc with excellent selectivity over iron and good solubility in the solvent ESCAID 100.

EXAMPLE 6

To a solution of phosphorus trichloride (55 g) in dry diethyl ether (200 cm$^3$) stirred and maintained at between −25° C. and −30° C. in an atmosphere of dry nitrogen a 2 molar solution of tert-butyl magnesium chloride in diethyl ether (200 cm$^3$, solution supplied by Aldrich Chemical Co.) was added during 45 min. After a further 30 min., a 2 molar solution of n-butyl magnesium chloride (200 cm$^3$, solution supplied by Aldrich Chemical Co.) was added in the same way. The suspension was stirred at −25° C. for a further 45 min., then allowed to reach ambient temperature, and finally boiled under reflux for 30 min., cooled, filtered to remove magnesium chloride, and distilled, yielding n-butyl tert-butyl chlorophosphine (30.8 g), b.p. 76°–78° C. under a pressure of 15 mm of mercury.

To the chlorophosphine prepared as described above (29.8 g), hexamethyldisilazane (13.3 g) was added at ambient temperature in an atmosphere of nitrogen and the solution was stirred and heated at 100° C. for 18 hr with distillation of chlorotrimethylsilane. The solution was cooled and toluene (50 cm$^3$) and sulphur (5.3 g) were added causing the temperature to rise to 90° C. The solution was heated at 100° C. for a further 4 hr. The solvent was distilled under reduced pressure yielding N-(n-butyl-tert-butylphosphinothioyl)-P-n-butyl-P-tert-butyl phosphinothioic amide, which solidified on cooling and was recrystallised from hexane yielding 3.8 g of white solid ($^{31}$P NMR in CDCl$_3$, singlet 89.2 ppm downfield of H$_3$PO$_4$; the solid is believed to be a substantially pure geometrical isomer, a second isomer showing a singlet at 87.7ppm being recoverable from the hexane solution). The purity was determined by titration of a sample dissolved in 50% tetrahydrofuran—water with 0.1M aqueous sodium hydroxide solution for the acidic (NH or SH) proton, which was 50% neutralised at pH 8.8; by this method the purity was found to be 94.5% of theoretical based on molecular weight 369. The product of Formula I in which $R^1=R^3$=n-butyl and $R^2=R^4$=tertbutyl was examined as an extractant by Test 2, with the result listed in Table 2 which shows that it is a strong extractant for zinc.

EXAMPLE 7

To a solution of phosphorus trichloride (55 g) in dry diethyl ether (200 cm$^3$) stirred and maintained at between –25° C. and –30° C. in an atmosphere of dry nitrogen, a 2 molar solution of tert-butyl magnesium chloride in diethyl ether (200 cm$^3$, solution supplied by Aldrich Chemical Co.) was added during 45 min. After a further 15 min. a 2 molar solution of 2-butyl magnesium chloride (200 cm$^3$, solution supplied by Aldrich Chemical Co.) was added in the same way. The suspension was stirred at –25° C. for a further 45 min., then allowed to reach ambient temperature, and finally boiled under reflux for 30 min., cooled, filtered to remove magnesium chloride, and distilled, yielding 2-butyl-tert-butylchlorophosphine (47 g), b.p. 74° C. under a pressure of 15 mm of mercury.

To the chlorophosphine prepared as described above (27.1 g), hexamethyldisilazane (12.1 g) was added at ambient temperature in an atmosphere of nitrogen and the solution was stirred and heated at 100° C. for 24 hr with distillation of chlorotrimethylsilane. Toluene (50 cm$^3$) and sulphur (4.8 g) were added and the solution was heated at 100° C. for a further 4 hr. The solvent was distilled under reduced pressure yielding N-(2-butyl-tert-butylphosphinothioyl)-P-2-butyl-P-tert-butyl phosphinothioic amide, a pale yellow oil which solidified on long standing ($^{31}$P NMR in CDCl$_3$, multiplet 86.0 ppm downfield of H$_3$PO$_4$). The purity was determined by titration of a sample dissolved in 50% tetrahydrofuran—water with 0.1M aqueous sodium hydroxide solution for the acidic (NH or SH) proton, which was 50% neutralised at pH 7.7; by this method the purity was found to be 79% of theoretical based on molecular weight 369. The compound of Formula I in which $R^1=R^3$=2-butyl $R^2=R^4$=tertbutyl was examined as an extractant for zinc by Test 2, with the result listed in Table 2, which shows that it is a very strong extractant for zinc with good solubility in the solvent ESCAID 100.

EXAMPLE 8

Dry ammonia gas was bubbled through dichloromethane (250 cm$^3$) to give a saturated solution which was stirred while diphenyl chlorothiophosphate was added in portions during 15 min. After the addition was complete, the passage of ammonia was continued for a few minutes to ensure completion of the reaction. The mixture was filtered to remove ammonium chloride and concentrated by distillation of solvent yielding diphenyl thiophosphoramide (7.2 g, m.p. 108°–110° C. MS:m/z 265. $^{31}$p NMR in CDCl$_3$, singlet 59.0 ppm downfield of H$_3$PO$_4$)

Sodium hydride (4.8 g) was added under anhydrous conditions to a stirred solution of diphenyl thiophosphoramide (5.3 g) in tetrahydrofuran (100 cm$^3$). When evolution of hydrogen had ceased, diphenyl chlorothiophosphate (5.7 g) was added. After stirring at 25° C. for 1.5 hr. the reaction mixture was boiled under reflux for 4 hr. The solvent was distilled under reduced pressure and the residue was extracted with toluene (100 cm$^3$). The toluene solution was successively extracted with dilute hydrochloric acid (2M, two 50 cm$^3$ amounts) and water (three 50 cm$^3$ amounts) dried with magnesium sulphate, filtered and the solvent was distilled under reduced pressure. The residue (6.0 g) solidified on trituration with hexane and was recrystallised from hexane yielding tetraphenyl thioimidodiphosphate (3.6 g; m.p. 103°–105° C.; MS, m/e 513 $^{31}$P NMR in CDCl$_3$ singlet 46.8 ppm downfield of H$_3$PO$_4$). The purity was determined by titration of a sample dissolved in 50% tetrahydrofuran—water with 0.1M aqueous sodium hydroxide solution for the acidic (NH or SH) proton, which was neutralised at below pH 4; by this method the purity was found to be 99% of theoretical based on molecular weight 513. The compound of Formula I in which $R^1=R^2=R^3=R^4$=phenoxy was examined as an extractant for zinc by Tests 1 and 2, with the results listed in Tables 1 and 2 respectively, which show that it is a strong extractant for zinc with excellent selectivity over iron.

EXAMPLE 9

Thiophosphoryl chloride (17.0 g) was dissolved in toluene (250 cm$^3$) and triethylamine (21.5 g) was added. The solution was stirred at 20° C. and 2,4-dimethylphenol (24.4 g) was added in portions during 1 hr. The mixture was stirred for 2 hr. and then heated and stirred at 80° C. for a further 2 hr. and then cooled and filtered to remove triethylamine hydrochloride. The toluene was distilled under reduced pressure leaving bis(2,4-dimethylphenyl) chlorothiophosphate (oil, 30.6 g. $^{31}$P NMR in CDCl$_3$, singlet 54.57 ppm downfield of H$_3$PO$_4$).

Dry ammonia gas was bubbled through tetrahydrofuran (250 cm$^3$) to give a saturated solution which was stirred while bis(2,4-dimethylphenyl) chlorothiophosphate (12.0 g) was added in portions during 15 min. After the addition was complete, the mixture was stirred for a further 2 hr. and then filtered to remove ammonium chloride and concentrated by distillation of solvent yielding bis(2,4-dimethyldiphenyl) thiophosphoramide (11.1 g. $^{31}$P NMR in CDCl$_3$, singlet, 59.6 ppm downfield of H$_3$PO$_4$).

Sodium hydride (1.1 g) was added under anhydrous conditions to a stirred solution of bis(2,4-dimethylphenyl) thiophosphoramide (6.42 g) in tetrahydrofuran (250 cm$^3$). When evolution of hydrogen had ceased (2 hr.), bis(2,4-dimethylphenyl) chlorothiophosphate (6.81 g) was added during 15 min., the mixture then being heated to 65° C. and held at this temperature for 16 hr. The mixture was cooled and a little acetic acid was added to destroy any unreacted sodium hydride. The solvent was distilled and the residue was extracted with hexane (250 cm$^3$). The hexane solution was extracted with dilute hydrochloric acid (2M, 250 cm$^3$) and then successively with water (three 200 cm$^3$ portions), dried (Mg SO$_4$), filtered and concentrated by distillation of the solvent under reduced pressure yielding crude tetrakis(2, 4-dimethylphenyl) thioimidodiphosphate (9.6 g, $^{31}$P NMR in CDCl$_3$, singlet 46.9 ppm downfield of H$_3$PO$_4$ with minor shifts attributable to the amide and chloro starting materials). The purity determined by titration as in Example 8 was 58% of theoretical based on MW 625. The crude product may itself be used as a solvent extractant but on this occasion it was purified by chromatography on silica gel (Kieselgel 60H supplied by E Merck Company, Darmstadt) using hexane to elute the impurities and ethyl acetate/hexane to elute the product which was found to be of 84% theoretical purity (MS:m/z 625). The product of Formula I in which $R^1=R^2=R^3=R^4$=2,4-dimethylphenoxy respectively which show that it is a strong extractant for zinc with excellent selectivity over iron and good solubility in ESCAID 100.

EXAMPLE 10

Diethyl chlorothiophosphate (25.04 g, supplied by Aldrich Chemical Company Ltd.) was added dropwise with stirring to a saturated solution of ammonia in tetrahydrofuran (250 cm$^3$). Stirring was continued for two hr. The mixture was filtered to remove precipitated ammonium chloride and then concentrated by distillation of the solvent under reduced pressure to a yellow oil (diethyl thiophosphoramide, 21.0 g, $^{31}$P NMR in CDCl$_3$, singlet, 67.4 ppm downfield of H$_3$PO$_4$). Without further purification, this amide (8.5 g) was redissolved in tetrahydrofuran (250 cm$^3$) and sodium hydride (13.2 g of a 20% suspension in toluene) was added with stirring. When hydrogen ceased to be evolved, diethyl chlorothiophosphate (9.5 g) was added dropwise during 15 min. The mixture was stirred and heated at 65° C. for 2 hr. and then cooled and filtered. The solvent was distilled under reduced pressure leaving a yellow oil which was dissolved in dichloromethane (250 cm$^3$) and stirred with dilute sulphuric acid (1 molar to ensure that the pH of the suspension was less than pH 2). The organic phase was separated, dried with magnesium sulphate, filtered, and concentrated by distillation of solvent under reduced pressure yielding tetraethyl thioimidodiphosphate (11.2 g, $^{31}$P NMR in CDCl$_3$, singlet, 56.4 ppm downfield of H$_3$PO$_4$). The purity was determined by titration of a sample dissolved in 50% tetrahydrofuran—water with 0.1M aqueous sodium hydroxide solution for the acidic (NH or SH) proton, which was 50% neutralised at pH 6.1. By this method the purity was found to be 77% of theoretical based on molecular weight 321. The compound of Formula I in which $R^1=R^2=R^3=R^4$=ethoxy was examined as an extractant for zinc by Tests 1 and 2, with the results listed in Tables 1 and 2, which show that it is a weak extractant for zinc with high selectivity over iron.

EXAMPLE 11

In the manner of Examples 6 and 7, 2-butyl magnesium chloride (800 cm$^3$ of a 2M solution in diethyl ether supplied by Aldrich Chemical Co.) was reacted with phosphorus trichloride (110 g) in diethyl ether (450 cm$^3$) to give di-2-butylchlorophosphine (77.8 g, b.p. 84° C. at a pressure of 15 mm of mercury), and this compound was further reacted with hexamethyldisilazane and sulphur to give N-(di-2-butylphosphino thioyl)-P,P-di-2-butylphosphinothioic amide (m.p. 110°–114° C. $^{31}$p NMR in CDCl$_3$, multiplet 87.9 ppm downfield of H$_3$PO$_4$). In this compound of Formula I, $R^1=R^2=R^3=R^4$=2-butyl.

It has been found that the rate of extraction of zinc by some of the compounds of this invention is comparatively slow when judged by the rates normally found for extraction reagents used in commercial processes for copper and this is true of the compound of this Example. It has been discovered, however, that the rates of extraction of zinc by compounds of this type may be improved considerably by the addition of relatively small amounts of certain additives. Particularly useful in this respect are compounds which are known themselves to extract zinc rapidly under certain conditions, and particularly extractants and organic acids of a strongly surfactant nature such as alkyl and aryl sulfonic acids.

In order to demonstrate the effectiveness of various additives, a screening test was set up based on monitoring the rate of fall of pH of the aqueous phase as the zinc was extracted during the extraction process. The general equation for the extraction of zinc by the reagent (RH) can be represented as

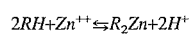
$$2RH + Zn^{++} \rightleftharpoons R_2Zn + 2H^+$$

Hence, as zinc ions in the aqueous phase are extracted they are replaced by protons liberated by the extractant. Thus, a rate of fall of pH is a reasonable indication of the rate at which a metal is being extracted. The amplified voltage output from a pH meter was applied to a flat bed recorder so as to be recorded as the ordinate. Time was represented on the abscissa. At the instant the organic phase was poured into the stirred aqueous solution, the motor driving the chart paper in the flat bed recorder was started and the drop of pH recorded as a function of time.

In all the rate experiments described here, two parts of an aqueous solution containing 5 g/l zinc as the sulphate at pH 2.0 were stirred vigorously under controlled conditions with one part of organic extractant formulation made up as described below.

The extractant compositions were based on a 0.1 molar solution (36.9 g/l) in a 1:9 ratio mix of chloroform and Escaid 100 of the tetraisobutyl compound product prepared as described above but containing small amounts of the additives as indicated below. It will be noted that in a number of cases the amount of additive used approximates to 1% by weight of the concentration of the extraction agent. In the table below, we record the times taken for the pH of the aqueous solution to fall from the initial pH of 2.0 to pH values of 1.7 and 1.6 as being a good indication of the effectiveness of some of the additive compounds at accelerating the rate of extraction of zinc. In all cases, the final pH value attained after a period of at least one hour was between 1.53 and 1.57 and it is apparent that this is close to being the equilibrium value.

The compounds investigated for this example were as follows:

| Experiment number | Additive | concentration (g/l) |
| --- | --- | --- |
| 1 | No additive | — |
| 2 | Didodecyl naphthalene sulphonic acid | 3.75 |
| 3 | Didodecyl naphthalene sulphonic acid | 0.46 |
| 4 | Sodiumdioctylsulphosuccinate | 0.37 |
| 5 | Di 2-ethylhexylphosphoric acid | 0.46 |
| 6 | Di 2,4,4 trimethylpentylthiophosphoric acid | 0.43 |
| 7 | The tetraphenoxy compound of Example 8 above | 0.42 |

The results are as shown in the table below:

| Experiment No | Time recorded for pH to fall to 1.7 | Time recorded for pH to fall to 1.6 |
| --- | --- | --- |
| 1 | 23 min | 43 min |
| 2 | <15 sec | <15 sec |
| 3 | 60 sec | 3.5 min |
| 4 | 60 sec | 3.5 min |
| 5 | 5.5 min | 11.5 min |
| 6 | 12 min | 24 min |
| 7 | 16 min | 32 min |

Clearly, all the additives tested in this example caused some acceleration of the rate of extraction as indicated by fall in pH, the most effective being the sulfonic acid compounds which, even when incorporated at concentrations approximately 1% by weight of the extractant, reduced extraction times to the order of a few minutes.

EXAMPLE 12

In order to demonstrate further the utility of materials of this invention for the extraction of metals, a study was made of the distribution of zinc as a function of various volume ratios of extractant and the aqueous metal bearing feed solution. This is a standard procedure in order to generate a distribution curve for an extractant and was performed by the following method. An organic solution was prepared containing 0.2 moles per liter of the extractant of Example 5 in the hydrocarbon solvent Escaid 100. The solution also contained 2 g per liter of didodecylnaphthalene sulphonic acid added to improve the rate of extraction in accord with the teaching of Example 10. Portions of this solution were stirred vigorously for a period of 1 hour at 25° C. and at different volume ratios with an aqueous zinc solution containing 5 g/l zinc as the sulphate at pH 2.0. The phases were then separated, filtered and each analysed for zinc content. The distribution of zinc between organic and aqueous phases after contacting at various volume ratios was found to be as follows.

| Volume organic contacted (ml) | Volume aqueous contacted (ml) | zinc in organic (g/l) | zinc in aqueous (g/l) |
| --- | --- | --- | --- |
| 40 | 10 | 1.295 | 0.16 |
| 20 | 10 | 2.365 | 0.34 |
| 10 | 10 | 3.90 | 1.22 |
| 10 | 20 | 5.36 | 2.46 |
| 10 | 40 | 5.74 | 3.62 |
| 10 | 80 | 5.96 | 4.35 |

In a solvent extraction process for recovery of a metal, it is essential that the extractant is not only capable of reducing the metal concentration in the aqueous feed to low levels but that the metal can be recovered subsequently from the organic phase by a stripping operation. Ideally with extractants of this type, stripping is carried out with an acidic aqueous solution such as a spent electrowinning electrolyte. In order to demonstrate this, a portion of the extractant solution of the composition described in the first part of this Example was loaded with zinc by contacting for 2 hours one part by volume with four parts by volume of an aqueous zinc solution containing 10 g/l zinc in sulphate solution at pH 2.15. The phases were then separated, the organic analysed and found to contain 5.84 g/l zinc.

Portions of this zinc loaded organic solution were then contacted at various volume ratios with an aqueous strip solution containing 30 g/l zinc and 180 g/l sulphuric acid. Contacting was carried out by vigorous stirring at 50° C. for a period of 2 hours. The phases were then separated and each analysed for zinc. The distribution of zinc after stripping at various volume ratios was found to be as follows.

| Volume aqueous contacted (ml) | Volume organic contacted (ml) | zinc in organic (g/l) | zinc in aqueous (g/l) |
| --- | --- | --- | --- |
| 20 | 10 | 1.32 | 33.5 |
| 7 | 15 | 1.65 | 41.7 |
| 5 | 20 | 2.04 | 49.5 |

EXAMPLE 13

An aqueous solution containing up to 350 parts per million of each of 13 different metals or metalloids and sufficient nitric acid to give a pH value of 2.0 was made up. The metals were taken as their nitrate or acetate salts except for arsenic which was taken as the trioxide. This solution was stirred rapidly with a 0.1 molar solution of the product of Example 5 that is N-(di-2-pentylphosphinothioyl)-P, P-di-2-pentylphosphinothioic amide made up in ESCAID 100, for one hour at 20°–25° C. The aqueous and organic phases were separated and each was analysed for metals content with the results tabulated below.

| | Concentration of metal found, in parts per million | |
| --- | --- | --- |
| Metal | In the aqueous phase | In the organic phase |
| iron(III) | 175 | 75 |
| chromium(III) | 260 | <5 |
| manganese(II) | 295 | <5 |
| zinc(II) | 15 | 335 |
| bismuth(III) | <5 | 135 |
| nickel(II) | 305 | <5 |
| arsenic(III) | 55 | <5 |
| calcium(II) | 271 | <5 |
| magnesium(II) | 300 | <5 |
| cadmium(II) | <5 | 295 |
| silver(I) | <5 | 340 |
| lead(II) | 90 | <5 |
| mercury(II) | <1 | 295 |

The results show that at an initial pH value as low as 2.0, zinc, bismuth, cadmium, silver, and mercury are strongly extracted and may be separated from the other metals listed.

EXAMPLE 14

4-sec-butylphenol (63 g) and phosphorus pentasulphide (22.2 g) were melted together under a flow of nitrogen gas, and the melt was stirred and heated at 120°–130° C. for 3 hours. During this time, evolved hydrogen sulphide was collected by passing the gas stream through aqueous sodium hydroxide solution. The melt was cooled to 60° C. and stirring was continued while sulphuryl chloride (27 g) was added dropwise during 45 minutes. Toluene (100 cm$^3$) was added, and the solution was allowed to cool, diluted with diethyl ether (400 cm$^3$) and extracted sequentially with ice-water (500 cm$^3$), 10% aqueous sodium carbonate (2×250 cm$^3$) and water (2×200 cm$^3$). The organic solution was separated and dried (MgSO$_4$) and concentrated under reduced pressure to a yellow oil (57.4 g) which was crude bis(4-sec-butyl-phenyl) chlorothiophosphate. All this chloro compound was reacted with ammonia as described in Example 9 to give bis(4-sec-butylphenyl) thiophosphoramide which was a solid and was recrystallised from hexane, m.p. 73°–74° C. (14.6 g).

The phosphoramide (9.43 g) and the chlorothiophosphate (9.91 g) both prepared as described above were reacted together with sodium hydride (80% suspension, 1.88 g) as described in Example 9 to give crude tetrakis (4-sec-butylphenyl) thioimidodiphosphate (14.9 g, 74.6% pure). The crude product was dissolved in hexane (200 cm$^3$) and extracted firstly with a mixture of methanol (180 cm$^3$) and saturated sodium bicarbonate solution (20 cm$^3$), and secondly with a mixture of methanol (180 cm$^3$) and saturated aqueous sodium carbonate solution (20 cm$^3$). It was shown by HPLC that the product resided only in the second extract, which was neutralised to pH 2 with dilute sulphuric acid and back-extracted into hexane (200 cm$^3$).

The hexane solution was then concentrated under reduced pressure to an oil (9.4 g) which was found, by titration as before, to be of 93.5% purity based on MW 737. The product of Formula I in which $R^1=R^2=R^3=R^4$=4-sec-butylphenoxy was examined as an extractant by Tests 1 and 2 with the results listed in Tables 1 and 2 respectively which show that it is a strong extractant for zinc with excellent selectivity over iron and good solubility in ESCAID 100.

TABLE 1

Results of Test 1:
Extraction of zinc and iron (in ppm) by a 0.2 molar solution of extractant in chloroform or ESCAID 100 from an aqueous solution containing 5 gpl of zinc and 7 gpl of ferric iron initially at pH 1.7 after stirring equal volumes of the solutions together for 1 hour.

| Extractant: product of Example number | Solvent chloroform | | Solvent ESCAID 100 | |
|---|---|---|---|---|
| | Zinc | Iron | Zinc | Iron |
| 1 | 860 | 30 | | |
| 2 | 580 | 10 | | |
| 3 initial pH was 1.9) | | | 30 | <5 |
| 4 | | | 11 | 4 |
| 5 | | | 252 | 9 |
| 8 | | | | |
| 9 | 205 | 3 | 2000 | 6 |
| 10 | 475 | 4 | 55 | <1 |
| 14 | | | 890 | 10 |

EXAMPLE 15

Sodium hydride (38.0 g of 80% suspension in mineral oil) was added to a stirred solution of 2-isopropylphenol (139.2 g) and thiophosphoryl chloride (84.5 g) in toluene (500 cm³) at such a rate that the reaction temperature did not rise above 65° C. After stirring for a further 0.5 hr at ambient temperature, the solution was extracted twice with water (250 cm³ portions), separated, dried (MgSO₄) and concentrated by distillation of solvents under reduced pressure yielding crude bis(2-isopropylphenyl) chlorothiophosphate, a brown oil (164.2 g); $^{31}$P NMR in CDCl₃, singlet 53.0 ppm downfield of H₃PO₄). Of this material, 54.0 g were reacted with ammonia by the procedure of Example 9 yielding crude bis(2-isopropylphenyl)thiophosphoramide (50.0 g; $^{31}$PNmr, singlet δ=58.8 ppm).

Sodium hydride (2.76 g of 80% suspension in mineral oil) was added to a stirred solution of the crude thiophosphoramide prepared as above (13.0 g) in hexane (100 cm³) and the mixture was stirred for 30 min. The crude chlorothiophosphate also described above (13.7 g) was then added and the mixture was stirred and boiled under reflux (65° C.) for 18 hr. After cooling to ambient temperature, sufficient isopropanol was added to destroy excess sodium hydride, and the strongly alkaline suspension was extracted with a mixture of methanol (190 cm³) and water (10 cm³). The methanol solution was separated, neutralised with dilute sulphuric acid to pH2, and back extracted with fresh hexane (300 cm³). The hexane solution was dried (MgSO₄) and concentrated by distillation of solvent under reduced pressure to an oil (12.5 g) in which the major component was tetrakis (2-isopropylphenyl) thioimido-diphosphate (NMR $^{31}$P, singlet, δ=46.8). The purity was estimated by titration as 55% based on MW 681. It was noted that poor yields and impure products were in general obtained in reacting thiophosphoramides derived from phenols having a bulky group in the ortho position. The product of Formula I in which $R^1=R^2=R^3=R^4$=2-isopropylphenoxy was examined as an extractant by Test 2 with with the result listed in Table 2 which shows it to be a strong extractant for zinc.

EXAMPLE 16

4-chloro-2-methylphenol (142.5 g) was dissolved in a mixture of hexane (200 cm³) and toluene (400 cm³) and sodium hydride (30.0 g of 80% suspension in mineral oil) was added. After stirring for 3 hrs, this suspension was added during 2 hr to a stirred solution of thiophosphoryl chloride (84.5 g) in hexane (100 cm³). The mixture was stirred for a further 18 hrs at ambient temperature, then diluted with ether (1000 cm³), filtered, and concentrated by distillation of solvents under reduced pressure yielding crude bis (4-chloro-2-methylphenyl) chlorothiophosphate, a brown oil (192 g) $^{31}$PNMR, singlet, 57 ppm). Some of this compound was converted to the thiophosphoramide by reaction with ammonia as described in Example 9 ($^{31}$PNMR, singlet 62.7 ppm) sodium hydride (2.07 g, 80% suspension) was added to a stirred solution of the thiophosphoramide (10.4 g) and the chlorothiophosphate (11.4 g) in dry tetrahydrofuran (50 cm³). Stirring at ambient temperature was continued for 18 hrs. The solvent was distilled under reduced pressure and the residue was taken up in hexane and the suspension was filtered. Purification by extraction into 5% aqueous methanol and back extraction as described in Example 15, gave tetrakis (4-chloro-2-methylphenyl) thioimidodiphosphate (9.4 g), ($^{31}$P NMR, singlet, 49.3 ppm) a brown oil of 81% purity as estimated by titration (MW711). The product of Formula I in which $R^1=R^2=R^3=R^4$=4-chloro- 2-methylphenoxy was examined as an extractant by Tests 2 and 3 with the results listed in Tables 2 and 3 respectively, which show that it is a stronger extractant for zinc than the substituted phenoxy derivatives of Examples 9, 14 and 15 and that it has has good selectively over iron.

EXAMPLE 17

The procedures of Example 16 were used to prepare tetrakis (4-chlorophenyl) thioimidodiphosphate from 4-chlorophenol. The product of Formula I in which $R^1=R^2=R^3=R^4$=4-chlorophenoxy was found to have a purity of 77% (MW 651) and was evaluated by Test 2 with the result listed in Table 2 which shows that it is a strong extractant for zinc, but not as strong as the product of Example 16.

EXAMPLE 18

General Method Applicable to Examples 18 to 34
A) Preparation of diphenylphosphonothioic chloride (Ph₂PS.Cl)
A mixture of chlorodiphenylphosphine (110.25 g) and thiophosphoryl chloride (84.75 g) was heated at 80°–90° C. for one hour in an atmosphere of nitrogen. The product was fractionally distilled yielding firstly phosphorus trichloride and then diphenylphosphonothioic chloride 122.7 g, bp 160°–162° at 0.25 mm of mercury pressure.
B) Preparation of diphenylphosphonothioic amide (Ph₂PS.NH₂):
Ammonia gas was bubbled through a solution of diphenylphosphonothioic chloride (118 g) in tetrahydrofuran (600 cm³) with cooling to maintain a reaction temperature below 50° C. The reaction mixture was diluted with ether (300 cm³) and extracted twice with water (100 cm³ amounts) to remove ammonium chloride. The organic solution was separated and dried (MgSO₄) and the solvent distilled yielding diphenylphosphonothioic amide, a white crystalline solid (101.8 g).
C) Reaction of chloro compounds with amido compounds:

The amido compound (0.04 moles) was dissolved when possible in 100–200 cm$^3$ of hexane. Occasionally it was necessary to include tetrahydrofuran (indicated by THF in the Examples) as a co-solvent to achieve solubility. Sodium hydride (0.1 mole, 80% dispersion in mineral oil) was added in nitrogen atmosphere to the stirred solution, the mixture being heated if necessary at up to 60° to achieve reaction as judged by formation of hydrogen gas. The chloro compound (0.04 moles) dissolved in hexane (100 cm$^3$) was then added and if necessary to complete the reaction as judged by HPLC the temperature was raised to 60° C. for up to 3 hours. Excess sodium hydride was decomposed by addition of isopropanol (up to 25 cm$^3$). The product was obtained in either of two ways:

i) the solvents were distilled and the residue was taken up in a water immiscible solvent (hexane or ethyl acetate), shaken with sufficient aqueous acid (2M HCl) to neutralise to pH2, extracted with water, dried (MgSO4) and concentrated by distillation of solvent under reduced pressure.

ii) the reaction solution was extracted with a mixture of methanol (190 cm$^3$) and water (10 cm$^3$) so as to extract the product as its sodium salt. The methanol solution was neutralised to pH 2 with hydrochloric acid and back extracted with fresh hexane. The hexane solution was concentrated by distillation of solvent under reduced pressure yielding the neutralised product as the distillation residue.

D) Preparation of amido compounds from chloro compounds.

Carried out as described in Example 9.

E) $^{31}$P Nmr spectra were measured on chloroform solutions, the multiplicity of the resonance and the shift (δ) in ppm downfield of H$_3$PO$_4$ being recorded.

F) The purity of the products was determined by potentiometric titration of a sample dissolved in 50% tetrahydrofuran water with 0.1M sodium hydroxide solution for the acidic (NH or SH) proton.

EXAMPLE 19

Bis (2,4-dimethylphenyl) thiophosphoramide (Example 9) was reacted with diphenylphosphonothioic chloride (Example 18, A) by General Procedure C(i). The crude product yielded a white solid on trituration with a little hexane which was the compound of Formula I in which $R^1=R^2$=phenyl and $R^3=R^4$=2,4-dimethylphenoxy. Yield, 11.6 g(54% of theoretical) titration purity 89%; $^{31}$PNMR, singlet 53 ppm; MS, m/z 537. Test 2 (Table 2) showed that the product is a strong extractant for zinc.

EXAMPLE 20

Bis (3-methoxyphenyl) chlorothiophosphate was prepared by reacting 3-methoxphenol with phosphorus pentasulphide and sulphuryl chloride by the method described in Example 14, and further reacted with ammonia by the procedure of Example 9 to give bis(3-methoxyphenyl) thiophosphoramide. This compound was reacted with diphenylphosphonothioic chloride using General Procedure C(ii) yielding the compound of Formula I in which $R^1=R^2$=phenyl and $R^3=R^4$=3-methylphenoxy. Yield 47%; titration purity 69%; $^{31}$PNMR, doublet, 49 ppm. Test 2 (Table 2) showed that the product is a strong extractant for zinc.

EXAMPLE 21

Commercial grade 4-t-nonylphenol (in which the nonyl groups are mixed and branched, 88.0 g) was dissolved in tetrahydrofuran (150 cm$^3$ and sodium hydride (12 g of 80% suspension) was added portionwise (frothing occurred). After 30 min. the suspension was added during 1 hr to a solution of thiophosphoyl chloride (33.9 g) maintained at −40° C. by external cooling in nitrogen atmosphere. The mixture was allowed to reach ambient temperature, diluted with hexane (300 cm$^3$) and extracted successively with water (3×100 cm$^3$) and methanol:water, 95:5 (3×100 cm$^3$). The hexane solution was dried (MgSO$_4$) and concentrated by-distillation under reduced pressure yielding bis(4-t nonylphenyl) chlorothiophosphate (52.3 g); $^{31}$pNMR, broad singlet, 58 ppm). This chloro compound was reacted with diphenylphosphonothioic amide (Example 18 B) by the General Method C(ii) (THF) yielding the compound of Formula 1 in which $R^1=R^2$=phenyl and $R^3=R^4$=4-t-nonylphenoxy. Yield 68% of theoretical; titration purity 75%, MW733; 31pNMR multiplet, 54 ppm that the product is a strong extractant for zinc with good solubility in hydrocarbon solvents.

EXAMPLE 22

This Example illustrates sequential reaction of thiophosphoryl chloride at low temperature to give a mixed diaryl chlorothiophosphate.

To a solution of thiophosphoryl chloride (33.9 g) in tetrahydrofuran (100 cm$^3$) stirred and externally cooled to −40° C. were added firstly during 30 min. a solution prepared by reacting 2,4-dimethylphenol (24.4 g) with sodium hydride (6.0 g, 80% suspension) in tetrahydrofuran (200 ml) and secondly after a further 10 minutes a solution prepared by reacting commercial grade 4-t-nonylphenol (44.0 g) with sodium hydride (6.0 g) in tetrahydrofuran (200 cm$^3$). The mixture was allowed to warm to room temperature when HPLC indicated that substantially one product had been formed. The mixture was diluted with ether (400 cm$^3$), extracted with water (3×100 cm$^3$), dried (MgSO$_4$) and concentrated yielding an oil (79.9 g) which was substantially 0-(2,4-dimethylphenyl)-0-(4-t -nonylphenyl) chlorothiophosphate. This compound was reacted with diphenylphosphonothioic amide using General Method C(ii) (THF), yielding the compound of Formula I in which $R^1=R^2$=phenyl, $R^3$=2,4-dimethylphenoxy and $R^4$=4-t nonylphenoxy. Yield 70%; titration purity 90%; MW635; $^{31}$PNMR, singlet, 53 ppm. Test 2 (Table 2) showed the product to be a strong extractant for zinc with good solubility in hydrocarbon solvents.

EXAMPLE 23

2-isopropyl-5-methylphenol was reacted with sodium hydride and thiophosphoryl chloride using the procedure of Example 21 to form bis(2-isopropyl-5-methylphenyl) chlorothiophosphate ($^{31}$PNMR, singlet, 57 ppm). This compound was reacted with diphenylphosphonothioic amide by the General Method C(ii) (THF) yielding the compound of Formula I in which $R^1=R^2$=phenyl and $R^3=R^4$=2-isopropyl-5-methylphenoxy. Yield 63%; titration purity, 90%, MW593; $^{31}$PNMR, quartet 53 ppm. Test 2 (Table 2) showed that the product is a very strong extractant for zinc; however on long standing it crystallised from ESCAID solution.

EXAMPLE 24

2-sec-butylphenol was used to prepare bis(2-sec-butyl-phenyl) chlorothiophosphate by the procedure of Examples 23 and 21. This compound was reacted with diphenylphosphonothioic amide by the General Method C(ii)

(THF) yielding the compound of Formula I in which $R^1=R^2$=phenyl and $R^3=R^4$=2-Sec-butylphenoxy. Yield 47%, titration purity 91%; MW593; $^{31}$PNMR, multiplet, 53 ppm. Test 2 (Table 2) showed that the product is a strong extractant for zinc.

EXAMPLE 25

2-Methoxyphenol was used to prepare bis(2-methoxyphenyl) chlorothiophosphate by the procedure of Examples 23 and 21. This compound was reacted with diphenylphosphonothioic amide by General Method C(ii) (THF), yielding the compound of Formula I in which $R^1=R^2$=phenyl and $R^3=R^4$=2-methoxyphenoxy. Yield 65%, titration purity 85%; MW541; Test 2 (Table 2) showed that the product is a fairly strong extractant for zinc.

EXAMPLE 26

Diethylthiophosphoramide (Example 10) was reacted with diphenylphosphonothioic chloride (Example 18, A) by General Method C(i) to give the compound of Formula I in which $R^1=R^2$=phenyl and $R^3=R^4$=ethoxy, which crystallised on trituration with hexane, titration purity 100%; MW385; $^{31}$PNMR two doublets, 63.2, 62.5 ppm and 52.1, 52.4 ppm. Test 2 (Table 2) showed that the product is a fairly strong extractant for zinc.

EXAMPLE 27

0,0-Bis(1,3-dimethylbutyl) phosphorodithioate (a commercial sample supplied by ICI Americas, 150 g) was externally cooled to less than 5° C. while sulphuryl chloride (101.3 g) was added during 1 hour. The solution was stirred for 1 hour at ambient temperature and then sulphur chlorides and other volatile materials were distilled by heating at 80° C. under a pressure of 0.2 mm of mercury. The residue was crude bis(1,3-dimethylbutyl) chlorothiophosphate (148 g; $^{31}$PNMR, singlets at 65.5, 65.9 and 66.2 ppm). It was further reacted with ammonia using the procedure of Example 9 to give bis(1,3-dimethylbutyl) thiophosphoramide, which was reacted with diphenylphosphonothioic chloride using General Method C(ii) to give the compound of Formula I in which $R^1=R^2$=phenyl and $R^3=R^4$=1,3-dimethylbutoxy. Yield (final stage) 14%; titration purity 75%, MW497. $^{31}$PNMR singlet, 47 ppm and multiplet, 55 ppm. Test 2 (Table 2) showed that the product is a strong extractant for zinc having good solubility in ESCAID 100.

EXAMPLE 28

Phenylphosphonothioic dichloride (52.8 g) was dissolved in tetrahydrofuran (50 cm$^3$) and stirred and maintained between −40° C. and −50° C. whilst a solution prepared by reacting 4-t-nonylphenol (55.0 g) with sodium hydride (80% dispersion, 7.5 g) in tetrahydrofuran (200 cm$^3$) was added dropwise during 1 hour. The reaction mixture was allowed to reach ambient temperature and then diluted with ether (400 cm$^3$) and extracted with water (3×75 cm$^3$). The ether solution was dried (MgSO$_4$) and concentrated by distillation of solvent under reduced pressure to an oil (84.3 g) which was 0-(4-t-nonylphenyl) phenylphosphorothioic chloride ($^{31}$PNMR, multiplet, 83.7). This compound (37.5 g) was dissolved in ether (300 cm$^3$) and ammonia was bubbled through the solution until HPLC showed that all had reacted. The mixture was then extracted with water (3×75 cm$^3$), dried (MgSO$_4$) and concentrated by distillation of solvent under reduced pressure to give 0-(4-t-nonylphenyl)phenylphosphorothioic amide (341 g; 31PNMR multiplet, 72.8 ppm).

The chloro compound and the amide prepared as described above were then reacted together using General Method C(ii) yielding the compound of Formula I in which $R^1=R^3$=phenyl and $R^2=R^4$=4-t-nonylphenoxy. Yield 40%; titration purity 70%; MW733; $^{31}$PNMR, multiplet 66.2 ppm. Test 2 (Table 2) showed that the product is a strong extractant for zinc with good solubility in ESCAID 100.

EXAMPLE 29

0-(4-t nonylphenyl) phenylphosphorothioic chloride (Example 28) was reacted with diphenylphosphonothioic antide (Example 18B) using he General Method C(ii). In this case however the product was not extracted into the aqueous methanol phase during final purification but remained in the hexane phase. The hexane was therefore extracted successively with 2M aqueous hydrochloric acid (2×200 cm$^3$) and water (2×200 cm$^3$) and then dried (MgSO$_4$) and concentrated under reduced pressure yielding the compound of Formula I in which $R^1=R^2= R^3$=phenyl and $R^4$=4-t-nonylphenoxy. Yield, 75%; titration purity 82%; MW951; $^{31}$PNMR, multiplets at 70 and 52 ppm; MS, m/z 59. Test 2 (Table 2) showed that the product is a strong extractant for zinc with good solubility in ESCAID 100.

EXAMPLE 30

Using the method of Example 28, 2-isopropyl-5-methylphenol was reacted with sodium hydride and then with one equivalent of phenylphosphonothioic dichloride to form 0-(2-isopropyl-5-methylphenyl) phenylphosphorothioic chloride, which was further reacted with ammonia, but using in this case tetrahydrofuran as the solvent, to form 0-(2-isopropyl-5-methylphenyl) phenylphosphorothioic amide. This amide was then reacted with bis(2-isopropyl-5-methylphenyl) chlorothiophosphate, which is described in Example 23, using the General Method C(ii) (THF) giving the compound of Formula I in which $R^1$=Phenyl and $R^2=R^3=R^4$= 2-isopropyl-5-methylphenoxy. Yield 48%; titration purity 88%; MW 665; $^{31}$PNMR, doublet, 50 ppm and doublet 65 ppm. Test 2 (Table 2) showed that the product is a strong extractant for zinc with good solubility in ESCAID 100.

EXAMPLE 31

Using the method of Example 28, 2,6-diisopropylphenol was reacted with sodium hydride and then with 1 equivalent of phenylphosphonothioic dichloride to form 0-(2,6-diisopropylphenyl) phenylphosphorothioic chloride. This chloro compound was reacted with diphenylphosphonothioic amide (Example 18B) using the General Method C(ii) (THF) with the difference that reaction in this case was slower requiring 5 hrs at 60° C. to reach completion. The product, a white solid having limited solubility in hexane, was the compound of Formula 1 in which $R^1=R^2=R^3$= phenyl and $R^4$=2,6-diisopropylphenoxy. Yield 72%, titration purity 88%; MW549; $^{31}$PNMR, doublet, 72 ppm and doublet 52 ppm. Test 2 (Table 2) showed that the product is a strong extractant for zinc.

EXAMPLE 32

2-isopropyl-4-t-nonylphenol was prepared as follows: a mixture of 2-isopropylphenol (272 g), propylene trimer (252 g), FULCAT 22B (a Fullers Earth Catalyst supplied by Laporte Industries 5.4 g), and phosphoric acid (4 drops) was stirred and heated at 80°–90° C. for 48 hours. Further additions of FULCAT 22B (5.4 g) and phosphoric acid (4 drops) were made and the reaction temperature was increased to 90°–100° C. for a further 72 hours. The mixture was cooled and filtered and fractionally distilled yielding 2-isopropyl-4-t-nonylphenol (301 g), b.p.148°–150° at 0.2 mm of mercury pressure.

The procedure of Example 21 was then used, except that 4-t-nonylphenol was replaced by an equivalent amount of 2-isopropyl-4-t-nonylphenol and in consequence the final product was not extracted into the methanolic phase in the purification step, but remained in the hexane phase. The product was the compound of Formula 1 in which $R^1=R^2=$ phenyl and $R^3=R^4=$2-isopropyl-4-t-nonylphenoxy. Yield, 59%; titration purity 80%, MW817, $^{31}$PNMR, multiplet, 53 ppm. Test 2 (Table 2) showed the product to be a stronger extractant for zinc than the product of Example 21 and that it has good solubility in ESCAID 100 .

EXAMPLE 33

2-Methyl-4-t-nonylphenol was prepared from 2-methylphenol (216 g) and propylene trimer (252 g) by the method described in Example 32 except that the reaction mixture was worked up and distilled after a reaction period of only 48 hours at 80° C. Yield, 245 g; bp 114°–132° C. at 0.2–0.3mm of mercury pressure.

The procedure of Example 22 was then repeated with the difference that an equivalent amount of 2-methyl-4-t-nonylphenol was used instead of 4-t-nonylphenol. The product was the compound of Formula 1 in which $R^1=R^2=$phenyl $R^3=$2,4-dimethoxyphenoxy and $R^4=$2-methyl-4-t-nonylphenoxy. Yield 50%; titration purity 89%, MW646; $^{31}$PNMR, multiplet, 53 ppm. Test 2 (Table 2) showed that the product is a stronger extractant for zinc than the product of Example 22, and that it has good solubility in ESCAID 100.

EXAMPLE 34

0-(2-isopropyl-5-methylphenyl) phenylphosphorothioic chloride and 0-(2-isopropyl-5-methylphenyl) phenylphosphorothioic amide which are both described in Example 30 were reacted together using the General Method C(ii) (THF) to give the Compound of Formula 1 in which $R^1$ and $R^3$ =phenyl and $R^2=R^4=$2-isopropyl-5-methylphenoxy. Yield 67%; titration purity 92%, MW593; $^{31}$PNMR, doublet, 65 ppm. Test 2 (Table 2) showed that the product is a strong extractant for zinc.

TABLE 2

Results of Test 2:
Amount of zinc extracted in parts per million at equilibrium on contacting a 0.2 molar solution of the extractant in chloroform or ESCAID 100 with an equal volume of 0.1 molar aqueous zinc sulphate solution (6540 ppm Zn) initially at pH 2.

| Extractant: product of Example number: | Zinc extracted (ppm) | | |
|---|---|---|---|
| | Solvent chloroform | Solvent ESCAID 100 | Other Solvents |
| 1 | 3170 | | |
| 2 | 2150 | | |
| 5 | 1760 | 4030 | |
| 6 | 2340 | | |
| 7 | 3900 | 5530 | |
| 8 | 1110 | | |
| 9 | | 2550 | |
| 10 | 200 | | |
| 14 | | 2020 | |
| 15 | | 2600 | |
| 16 | | 3380 | |
| 17 | | 2280 | |
| 19 | 2600 | | |
| 20 | | | 2600 (Escaid/chloroform) 60/40 |
| 21 | 1760 | 3450 | 3190 (Solvesso 150) |
| 22 | | 3580 | 3380 (Solvesso 150) |
| 23 | 2540 | 4420 | 4290 (Solvesso 150) |
| 24 | 2470 | | |
| 25 | 520 | | 1820 (Solvesso 150) |
| 26 | 520 | | |
| 27 | | 2740 | |
| 28 | | 2080 | |
| 29 | 1370 | 3120 | |
| 30 | | 2930 | |
| 31 | 1300 | | |
| 32 | | 4100 | |
| 33 | | 3900 | 3700 (Solvesso 150) |
| 34 | | | 2400 (Solvesso 150) |

EXAMPLE 35

The ability of a number of compounds of the invention to extract zinc with high selectivity over iron from feed solutions containing high concentrations of metals is further illustrated by the following test:
TEST 3

An aqueous solution was prepared simulating a real leach solution which contained:
20.1 gpl zinc, 12.5 gpl ferric iron, 0.47 g/calcium, 2.6 g/l magnesium taken as the sulphates at a pH of 1.8. Portions of this aqueous solution were equilibrated with twice the volume of a 0.5 molar solution (in ESCAID 100 or SOLVESSO 150) of the compounds to be tested by vigorous stirring at room temperature for a period of 24 hours. The organic and aqueous phases were then separated, filtered and each analysed for zinc and iron by inductively coupled plasma (ICP) spectrophotometry. The results given in Table 3 confirm that organic solutions of each compound extract substantial quantities of zinc with high selectivity over iron.

TABLE 3

Results of Test 3
Extraction of zinc (gpl) and iron (ppm) by 0.5 molar solutions of extractant in organic solvent.

| Extractant - Product of Example No: | Solvent | Zinc (gpl) | Iron (ppm) |
|---|---|---|---|
| Example 5 (Note 1) | Escaid 100 | 13.6 | 60 |
| Example 29 | Solvesso 150 | 10.58 | 525 |
| Example 22 | Solvesso 150 | 11.6 | 295 |
| Example 30 | Escaid 100 | 12.0 | 65 |
| Example 16 | Escaid 100 | 12.3 | 115 |

Note 1: In this case, the Extractant solution contained dinonylnaphthalene sulphonic acid (5% by weight of the pure extractant) included as a rate catalyst in accordance with the teaching of Example 11, and the period of contact was 15 minutes only, at a temperature of 40° C.

EXAMPLE 36

As in Example 12, the utility of the products of the invention in zinc recovery processes was shown by demonstrating that the zinc may be recovered from the organic phase by stripping with an aqueous solution which in this case was chosen to simulate a spent zinc electrowinning electrolyte. For each product to be tested, a 0.5 molar solution of the product in ESCAID 100 (or SOLVESSO 150 if noted in Table 4) was loaded with zinc by contact with the aqueous feed solution used in Example 35. Portions of this zinc loaded organic solution were then contacted at various volume ratios with an aqueous strip solution containing 30 gpl zinc as zinc sulphate and 180 gpl sulphuric acid. Contacting was carried out by vigorous stirring at 50° C. for 2 hours. The aqueous and organic phases were then separated and each was analysed for zinc. The distribution of zinc after stripping the extractants at various volume ratios is shown for each product in Table 4. As in Example 35, the rate catalyst dinonyl naphthalene sulphonic acid (5% by weight of pure extractant) was included in the solution of the product of Example 5. The results listed in Table 4 show that zinc may be efficiently stripped from the organic solutions by a strongly acidic solution even when it contains initially 30 gpl of zinc, and, by comparison with Example 35, that the weaker extractants are most efficiently stripped.

TABLE 4

Zinc stripping distribution data

| Extractant: Product of | Example No: | Volume ratio Organic: Aqueous Solution | | |
|---|---|---|---|---|
| | metal gpl | 1/2 | 2.14/1 | 4/1 |
| Example 5 | Zn in organic | 4.05 | 5.45 | 6.85 |
| | Zn in aqueous | 34.7 | 51.05 | 59.40 |
| Example 22 (Solvesso 150) | Zn in organic | 1.2 | 2.76 | 4.66 |
| | Zn in aqueous | 37.1 | 57.38 | 73.06 |
| Example 30 | Zn in organic | 1.13 | 2.36 | 4.02 |
| | Zn in aqueous | 37.06 | 61.75 | 78.25 |
| Example 16 | Zn in organic | 2.53 | 4.06 | 6.05 |
| | Zn in aqueous | 36.63 | 53.19 | 73.81 |

EXAMPLE 37

In order to demonstrate more fully the utility of an example of products of the invention in a zinc recovery process, a small scale solvent extraction process was operated in a continuous manner using a solution of the product described in Example 5 as extractant. The process employed mixer-settlers for the contacting and separation of the organic and aqueous phases and used 3 counter current stages for extraction and 3 counter current stages for stripping. The mixing chamber in each mixer-settler was of volume 125 ml, and the settling compartment had a volume of 375 ml. Flow rates were chosen to give organic to aqueous flow ratios of 3.0 in extraction and 4.7 in stripping with a mean mixer residence time in extraction of 5 minutes. Small heat exchangers were used to maintain a temperature of 40° C.±2° C. in each mixer settler.

The organic phase was a 0.5 molar solution of the product of Example 5 containing 2.5 g/l dinonylnaphthalene sulphonic acid as rate catalyst. The aqueous feed contained 22.9 gpl zinc and 3.9 gpl ferric iron as their sulphates at pH 2.0. Stripping was by an aqueous solution containing 70 gpl zinc as sulphate and 180 gpl sulphuric acid.

The process was operated continuously during the working day over a period of several days in order to allow concentrations to stabilise. Samples were then taken and analysed for zinc by atomic absorption spectrophotometry. It was found that the zinc level in the aqueous raffinate stream had been reduced to 5.2 gpl zinc, whereas the zinc level in the aqueous strip solution exiting the process had increased to 101.6 gpl, thus demonstrating the ability of this composition to extract zinc from the feed solution and to transfer it at higher concentration to the aqueous stripping solution.

We claim:

1. A compound of the formula:

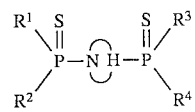

wherein each of $R^1$, $R^2$, $R^3$ and $R^4$ is a branched alkyl group containing from 3 to 20 carbon atoms.

2. A compound according to claim 1 wherein each of $R^1$, $R^2$, $R^3$ and $R^4$ is a secondary alkyl group.

3. A compound according to claim 1 wherein $R^1$, $R^2$, $R^3$ and $R^4$ taken together contain at least 16 saturated aliphatic carbon atoms.

4. A compound according to claim 3 wherein each of $R^1$, $R^2$, $R^3$ and $R^4$ is 2-pentyl.

5. A compound according to claim 3 wherein $R^1$, $R^2$, $R^3$ and $R^4$ taken together contain at least 20 saturated aliphatic carbon atoms.

* * * * *

UNITED STATES PATENT AND TRADEMARK OFFICE
CERTIFICATE OF CORRECTION

PATENT NO. : 5,502,250

DATED : March 26, 1996

INVENTOR(S) : CAMPBELL et al

It is certified that error appears in the above-identified patent and that said Letters Patent is hereby corrected as shown below:

Claim 1, Col. 28, line 40, change the formula from " 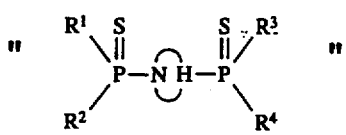 "

to -- 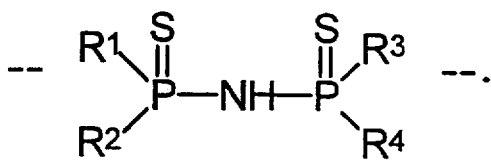 --.

Signed and Sealed this

Ninth Day of July, 1996

Attest:

BRUCE LEHMAN

Attesting Officer

Commissioner of Patents and Trademarks